(12) United States Patent
Oganesyan et al.

(10) Patent No.: US 10,597,664 B2
(45) Date of Patent: *Mar. 24, 2020

(54) EXPRESSION AND PURIFICATION OF CRM PROTEINS AND RELATED PROTEINS, AND PROTEIN DOMAINS

(71) Applicant: Fina BioSolutions, LLC, Rockville, MD (US)

(72) Inventors: Natalia Oganesyan, North Potomac, MD (US); Andrew Lees, Silver Spring, MD (US)

(73) Assignee: Fina BioSolutions, LLC, Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/154,020

(22) Filed: Oct. 8, 2018

(65) Prior Publication Data

US 2019/0032063 A1 Jan. 31, 2019

Related U.S. Application Data

(63) Continuation-in-part of application No. 15/114,642, filed as application No. PCT/US2015/014130 on Feb. 2, 2015, now Pat. No. 10,093,704.

(60) Provisional application No. 61/934,377, filed on Jan. 31, 2014.

(51) Int. Cl.
| | |
|---|---|
| *A61K 39/00* | (2006.01) |
| *A61K 39/385* | (2006.01) |
| *A61K 39/02* | (2006.01) |
| *A61K 39/40* | (2006.01) |
| *A61K 48/00* | (2006.01) |
| *A01N 63/00* | (2020.01) |
| *C12N 15/70* | (2006.01) |
| *C07K 14/34* | (2006.01) |
| *C07K 1/22* | (2006.01) |
| *C07K 14/33* | (2006.01) |
| *C07K 14/235* | (2006.01) |
| *A61K 47/60* | (2017.01) |
| *C12N 9/02* | (2006.01) |
| *C12N 9/06* | (2006.01) |
| *A61K 38/00* | (2006.01) |

(52) U.S. Cl.
CPC .............. *C12N 15/70* (2013.01); *A61K 47/60* (2017.08); *C07K 1/22* (2013.01); *C07K 14/235* (2013.01); *C07K 14/33* (2013.01); *C07K 14/34* (2013.01); *C12N 9/003* (2013.01); *C12N 9/0051* (2013.01); *A61K 38/00* (2013.01); *C12N 2830/30* (2013.01)

(58) Field of Classification Search
CPC ......... C12P 21/02; C07K 14/34; A61K 39/05; C12N 15/74; G01N 33/6803
See application file for complete search history.

(56) References Cited

U.S. PATENT DOCUMENTS

| | | | | |
|---|---|---|---|---|
| 10,093,704 B2* | 10/2018 | Oganesyan | ............ | C07K 14/34 |
| 2004/0043468 A1 | 3/2004 | Mauro | | |
| 2004/0063187 A1 | 4/2004 | Roemisch et al. | | |
| 2006/0030022 A1 | 2/2006 | Beckwith | | |
| 2007/0254334 A1 | 11/2007 | Beckwith et al. | | |
| 2011/0287443 A1* | 11/2011 | Retallack | ............... | C07K 14/34 435/7.1 |
| 2015/0184215 A1* | 7/2015 | Hsu | ........................ | C07K 14/34 435/69.1 |

OTHER PUBLICATIONS

Zhao et al., Chinese Journal of Cellular and Molecular Immunology, Nov. 2003;19(6):585-7. (Year: 2003).*
Tanito et al., Invest Ophthalmol Vis Sci., 2002; 43: 2392-2400.*
Examination Report for CN App. No. 201580018271.2 dated Jul. 9, 2019.
Examination Report for CN App. No. 201580018271.2 dated Jul. 9, 2019—translation.
Examination Report for CA App. No. 2,938,251, dated May 25, 2017.
Examination Report for CA App. No. 2,938,251, dated Jul. 12, 2019.
JPO Examination Report for JP 2016-567466, dated Jul. 5, 2018.
JPO Examination Report for JP 2016-567466, dated Jul. 5, 2018 (Translation).
EPO Examination Report for EP 15 743 243.6, dated Jun. 18, 2018.
EP Application No. 15 74 3243 Search Report dated Jun. 26, 2017.
EP Application No. 15 74 3243 Provisional Opinion Accompanying Search Report dated Jun. 26, 2017.
CA Exam Report for CA App. No. 2938251, dated May 25, 2017.
JPO Examination Report for JP 2016-567466 dated Mar. 14, 2019.
JPO Examination Report for JP 2016-567466 dated Mar. 14, 2019 (translation).
Examination Report for EP App. No. 15 743 243.6 dated Jul. 29, 2019.
EPO Examination Report for EP 15 743 243.6 dated Nov. 28, 2018.
CN Examination Report for CN Application No. 201580018271.2 dated Feb. 27, 2019.
CN Examination Report for CN Application No. 201580018271.2 dated Feb. 27, 2019 (translation).

(Continued)

*Primary Examiner* — Gary B Nickol
*Assistant Examiner* — Lakia J Jackson-Tongue
(74) *Attorney, Agent, or Firm* — Remenick PLLC

(57) ABSTRACT

The present invention is directed to the cells, compositions and methods for the production of recombinant protein. In particular, the invention is directed to a production process for obtaining high levels of soluble recombinant $CRM_{197}$ protein from *E. coli*. Cells preferably contain one or more mutations of disulfide reductase genes, so that disulfide reductase activity is reduced. The invention also relates to purification method for $CRM_{197}$ as well as characterization of properly folded $CRM_{197}$ protein.

68 Claims, 2 Drawing Sheets

Specification includes a Sequence Listing.

(56) References Cited

OTHER PUBLICATIONS

Study of the expression and purification of the diphtheria toxin variant CRM197 and the properties thereof, Xiao Jiagaimei, China Master's Theses Full-text Database, *Volume of medical and health science and technology*, E059-231, published Oct. 15, 2012 (in Chinese).

Influence of the Reductase Deficient *Escherichia coli* on the Solubility of Recombinant Proteins Produced in It, Xiong Sheng et al., *Chinese Journal of Biotechnology*, vol. 19.6:686-691, published Nov. 30, 2003 (in Chinese).

Soluble expression of recombinant human fibroblast growth factor-8a in *Escherichia coli*, Fu Can, *Journal of Heze University*, vol. 31:94-98, published Mar. 31, 2009 (in Chinese).

\* cited by examiner

EXPRESSION AND PURIFICATION OF CRM PROTEINS AND RELATED PROTEINS, AND PROTEIN DOMAINS

SEQUENCE LISTING

The instant application contains a Sequence Listing which has been submitted electronically in ASCII format and is hereby incorporated by reference in its entirety. Said ASCII copy, created on Feb. 11, 2015, is named 8164.014. PCT_SL.txt and is 14,566 bytes in size.

REFERENCE TO RELATED APPLICATIONS

This application is a continuation-in-part of U.S. application No. 15/h filed Jul. 27, 2016, which issued as U.S. Pat. No. 10,093,704 on Oct. 9, 2018, which is a National Stage Application, under 35 U.S.C. § 371, of International Application No. PCT/US2015/14130 filed Feb. 2, 2015, which claims priority to U.S. Provisional Application No. 61/934,377 filed Jan. 31, 2014, the entirety of each of which is specifically incorporated by reference.

BACKGROUND

1. Field of the Invention

The present invention relates to the field of recombinant protein production in bacterial hosts. In particular, the present invention relates to a production process for obtaining high levels of soluble recombinant $CRM_{197}$ protein from *E. coli*. The invention also relates to purification and characterization methods for $CRM_{197}$ as well as uses of the $CRM_{197}$ produced by the method.

2. Description of the Background

Diphtheria toxin (DT) is a proteinaceous exotoxin synthesized and secreted by pathogenic strains of *Corynebacterium diphtheriae*. These pathogenic strains contain a bacteriophage lysogen that carries the toxin gene. Diphtheria toxin is an ADP-ribosylating enzyme that is secreted as a proenzyme of 535 residues and processed by trypsin-like proteases with release of two fragments (A and B). Fragment A uses NAD as a substrate, catalyzing the cleavage of the N-glycosidic bond between the nicotinamide ring and the N-ribose and mediating the covalent transfer of the ADP-ribose (ADPRT activity) to the modified histidine 715 (diphthamide) of the elongation factor EF-2. This post-translational diphthamide modification inactivates EF-2, halting protein synthesis and resulting in cell death. The A fragment of DT (also named C domain) carries the catalytic active site and is the only fragment of the toxin required for the final step of intoxication. The R domain, carried on the B fragment, mediates binding to receptors on the host cell surface and the T domain, also carried on the B fragment, promotes the pH-dependent transfer of fragment A to the cytoplasm. An Arginine-rich disulfide-linked loop connects fragment A to fragment B (or domain C to domains TR). This inter-chain disulfide bond is the only covalent link between the two fragments after proteolytic cleavage of the chain at position 186. The isolation of various non-toxic and partially toxic immunologically cross-reacting forms of diphtheria toxins (CRMs or cross reacting materials) resulted in discovery of $CRM_{197}$ (Uchida et al., Journal of Biological Chemistry 248, 3845-3850, 1973; see also Giannini et al. Nucleic Acids Res. 1984 May 25; 12(10):4063-9). Preferably, CRMs can be of any size and composition that contain all or a portion of DT.

$CRM_{197}$ is an enzymatically inactive and nontoxic form of diphtheria toxin that contains a single amino acid substitution G52E. This mutation causes intrinsic flexibility of the active-site loop in front of the NAD-binding site and reduces the ability of $CRM_{197}$ to bind NAD and eliminates toxic properties of DT (Malito et al., Proc Natl Acad. Sci. USA 109(14):5229-342012) Like DT, $CRM_{197}$ has two disulfide bonds. One disulfide joins Cys186 to Cys201, linking fragment A to fragment B. A second disulfide bridge joins Cys461 to Cys471 within fragment B. Both DT and CRM197 have fragment A-associated nuclease activity (Bruce et al., Proc. Natl. Acad. Sci. USA 87, 2995-8, 1990).

$CRM_{197}$ is commonly used as the carrier protein for protein-carbohydrate and hapten-protein conjugates. As a carrier protein, $CRM_{197}$ has a number of advantages over diptheria toxoid as well as other toxoid proteins, many of which have been documented (Shinefield Vaccine, 28:4335, 2010, Broker et al, Biologicals, 39:195 2011). For example, since $CRM_{197}$ is genetically detoxified, it retains a larger complement of lysines, which are used for conjugation but are blocked by chemical toxoiding. $CRM_{197}$ has proven to be an effective carrier protein for *Streptococcus pneumonia* capsular polysaccharides, as evidenced by the success of PREVNAR™ (Pfizer), a vaccine consisting of up to 13 capsular polysaccharides chemically linked to $CRM_{197}$. There is also evidence suggesting that compared with tetanus toxoid, there is less carrier-induced suppression of the immune response, especially when there are many individual polysaccharides linked to the same carrier protein.

$CRM_{197}$ and native DT have a similar affinity for the diphtheria toxin receptor (DTR), which has an identical amino acid sequence to the HB-EGF precursor pro-HB-EGF (Mitamura et al., J. Biol. Chem. 272(43):27084-90, 1997). $CRM_{197}$ binds to the soluble form of HB-EGF, as well as to the membrane form pro-HB-EGF, and inhibits HB-EGF mitotic action by preventing its binding to EGF receptor. Thus $CRM_{197}$ may also have a future role in cancer therapy (Miyamoto et al., Anticancer Res. November-December 27(6A):3713-21, 2007).

$CRM_{197}$ has been produced in the original host *Corynebacterium*, but yields are low, typically <50 mg/L and, in addition, *Corynebacterium* growth is relatively slow as compared with, for example, *E. coli*. There are proprietary strains of *Corynebacterium* that have been engineered to produce $CRM_{197}$ at higher levels (U.S. Pat. No. 5,614,382). $CRM_{197}$ has also been expressed in a proprietary strain of *Psuedomonas fluorescens* and expressed at high levels. Production of $CRM_{197}$ in *E. coli* would be advantageous since *E. coli* is a BL1 level organism that is inexpensive to culture and propagate. Production of $CRM_{197}$ in *E. coli* has mainly resulted in insoluble inclusion bodies (generally insoluble), which then requires a difficult refolding process, resulting in low yields. A method for the overexpression of soluble tag free $CRM_{197}$ in *E. coli* suitable for the large quantity protein production, has not been reported. Thus, there is a need for better methods to produce $CRM_{197}$ in an efficient and cost-effective manner.

SUMMARY OF THE INVENTION

The present invention overcomes the problems and disadvantages associated with current strategies and designs and provide new compositions and methods for producing CRM.

One embodiment of the invention is directed to methods of producing all or a portion of a CRM protein, such as preferably CRM$_{197}$, comprising; providing a recombinant cell that contains an expression vector, wherein the recombinant cell has been modified to shift the redox status of the cytoplasm to a more oxidative state as compared to an unmodified recombinant cell and the expression vector contains an inducible promoter functionally linked to a CRM coding sequence, a spacer sequence between a ribosome binding site and an ATG codon, an expression enhancer region upstream of the CRM coding sequence; inducing the expression vector to produce CRM protein; and isolating the CRM protein expressed. The recombinant cell may be a eukaryotic cell or a prokaryotic cell. Preferably the recombinant cell is a prokaryotic cells such as, for example, an *E. coli* cell or a derivative or strain of *E. coli*. Preferably, the recombinant cell modification comprises a reduced activity of one or more disulfide reductase enzymes such as, for example, one or more of an oxidoreductase, a dihydrofolate reductase, a thioredoxin reductase, a protein reductase or a glutathione reductase. Preferably the reduced activity of the one or more disulfide reductase enzymes shifts the redox state of the cytoplasm of the recombinant cell to an oxidative state as compared with a non-recombinant cell. Preferably the CRM coding sequence encodes one or more CRM epitopes, CRM peptide sequences, CRM domains, or combinations thereof. Preferably the spacer comprises more or less than 9 nucleotides such as, for example, between 5 and 20 nucleotides. Preferably the expression enhancer comprises a ribosome binding site upstream of the CRM coding sequence and an ATG codon. Preferably the CRM protein expressed by the cell is soluble and is intracellular, periplasmic or secreted. Preferably the recombinant cell is propagated at a temperature from about 15° C. to about 32° C.

Preferably, the CRM protein is isolated from the cell by chromatography comprising, as a preferable chromatography medium, a dextran sulfate resin, a gel resin, an active sulfated resin, a phosphate resin, a heparin resin or a heparin-like resin.

Another embodiment of the invention is directed to CRM protein isolated by the methods of the invention. Preferably, the isolated CRM protein is conjugated and the conjugated CRM protein is formulated as a vaccine.

Another embodiment of the invention is directed to methods of producing all or a portion of a CRM protein such as for example a protein or peptide produced from a CRM coding sequence that encodes one or more CRM epitopes, CRM peptide sequences, CRM domains, or combinations thereof, and preferably CRM$_{197}$, comprising providing a recombinant cell that contains an expression vector, wherein the expression vector contains a promoter functionally linked to a CRM coding sequence; expressing CRM protein from the CRM coding sequence; and isolating the CRM protein expressed. Preferably the recombinant cell is a prokaryotic or a eukaryotic cell and preferably the prokaryotic cell is an *E. coli* cell or a derivative or strain of *E. coli*. Preferably the promoter is constitutive or inducible. Preferably the recombinant cell has been modified to shift the redox status of the cytoplasm to a more oxidative state as compared to an unmodified recombinant cell. Preferably the modified recombinant cell has reduced activity of one or more disulfide reductase enzymes such as, for example, one or more of an oxidoreductase, a dihydrofolate reductase, a thioredoxin reductase, a protein reductase or a glutathione reductase. Preferably the expression vector contains a spacer sequence between a ribosome binding site and an ATG codon such as, for example, wherein the spacer comprises more or less than 9 nucleotides and/or is between 5 and 20 nucleotides. Preferably the expression vector contains an expression enhancer such as, for example, a ribosome binding site upstream of the CRM coding sequence and an ATG codon.

Another embodiment of the invention is directed to methods for isolating and/or purifying CRM protein comprising: loading the CRM protein onto a chromatography column containing a resin with a loading buffer wherein the resin is preferably a dextran sulfate resin, a gel resin, an active sulfated resin, a phosphate resin, a heparin resin or a heparin-like resin; washing the resin with one or more washing buffers; and eluting CRM protein from the resin with an elution buffer. Preferably the loading buffer and the washing buffer are or contain the same components and at the same or in similar amounts. Preferably the loading buffer and the one or more washing buffers are low conductivity buffers such as, for example, a conductivity of about 10 mS/cm or less. Preferably the elution buffer is a high conductivity buffer such as, for example, a conductivity of about 10 mS/cm or more.

Another embodiment of the invention is directed to methods of characterizing folding of diphtheria toxin or CRM protein comprising: contacting diphtheria toxin or CRM protein to HB-EGF; determining the amount of binding of diphtheria toxin or CRM protein to HB-EGF; and determining the folding of diphtheria toxin or CRM protein by the amount of binding determined, wherein binding indicates correct folding. Preferably the diphtheria toxin or CRM contains a receptor binding domain. Preferably the CRM protein comprises CRM$_{197}$. Also preferably the at least one of the diphtheria toxin or CRM protein and/or the HB-EGF is bound to a solid support. Preferably the amount of binding of diphtheria toxin or CRM protein to HB-EGF is determined by an ELISA and the CRM protein that binds to HB-EGF is soluable in PBS.

Other embodiments and advantages of the invention are set forth in part in the description, which follows, and in part, may be obvious from this description, or may be learned from the practice of the invention.

DESCRIPTION OF THE INVENTION

Figure 1:
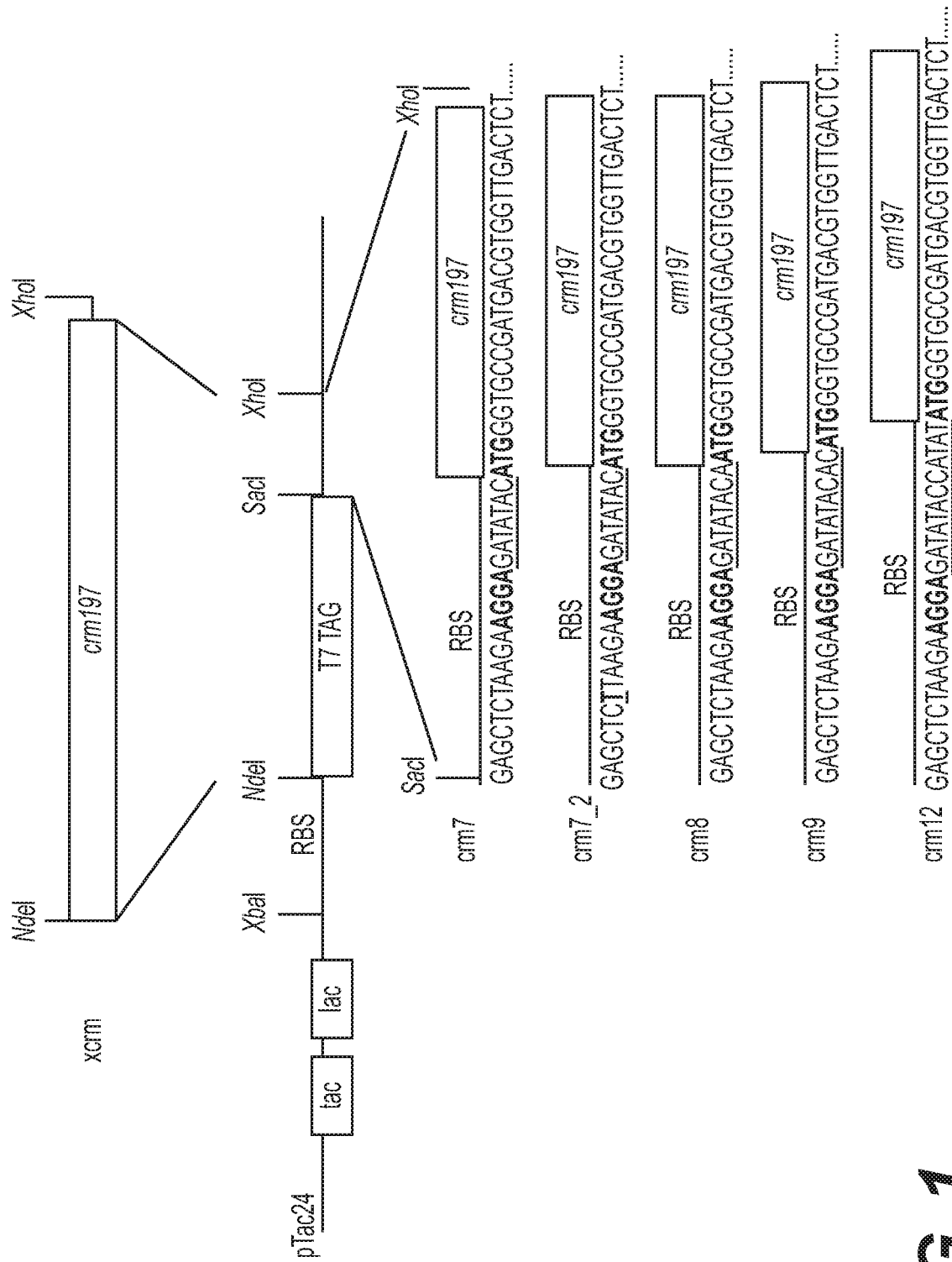
FIG. 1 Schematic of vector constructs crm7 (SEQ ID NO 10), crm7_2 (SEQ ID NO 11), crm 8 (SEQ ID NO 12), crm 9 (SEQ ID NO 13), and crm 12 (SEQ ID NO 14) with the ribosome binding site (RBS) and start codon (ATG) both indicated in bold with the spacer sequence underlined.
Figure 2:
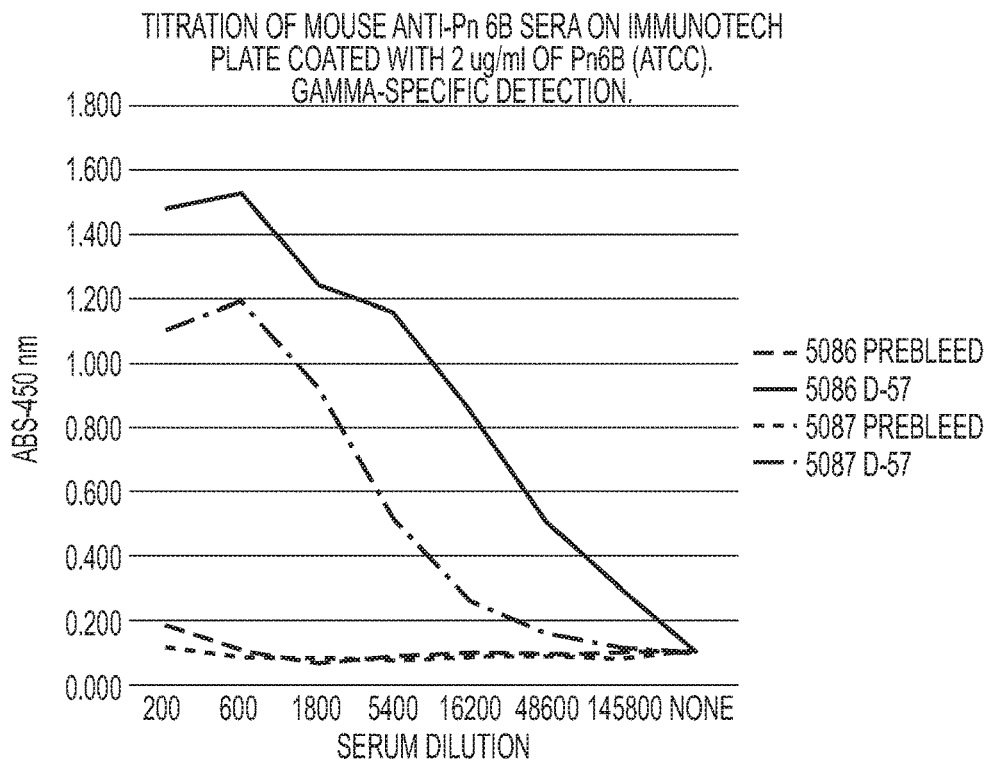
FIG. 2 Results of titration of mouse anti-pn6B sera on immunotech plates coated with 2 μg/ml of pn6B.
Figure 3:
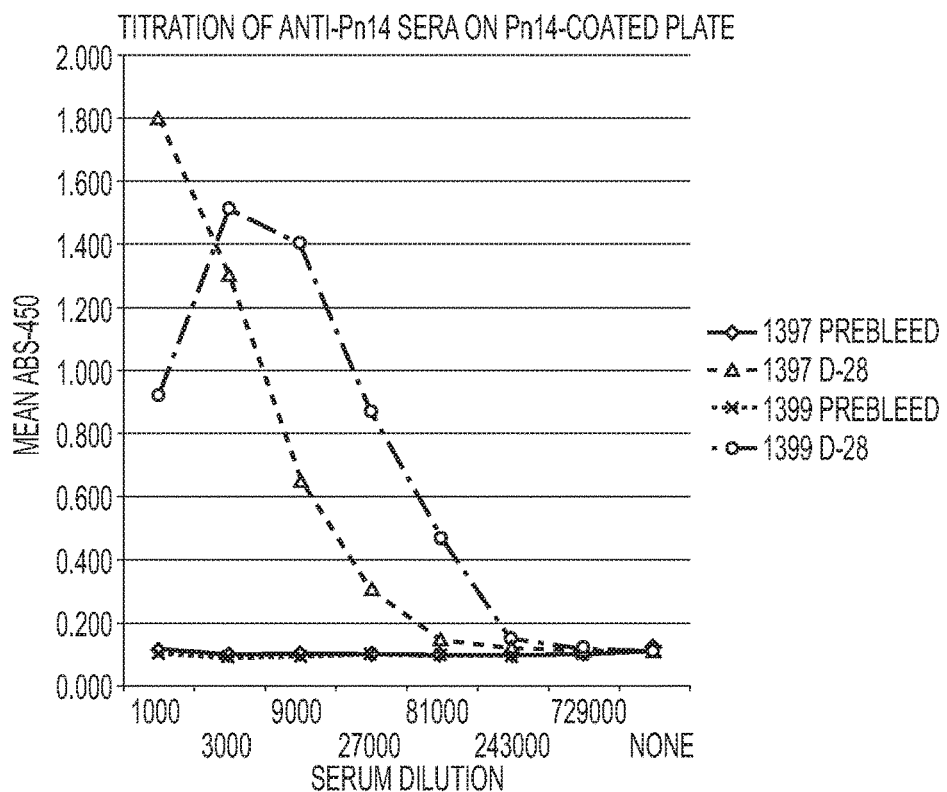
FIG. 3 Results of titration of anti-pn14 sera on pn14 coated plates.

Soluble, intact recombinant CRM$_{197}$ was first produced in protease-deficient *E. coli* (Bishai et. al 1987). However, the amount of protein production was very low. Subsequently, CRM$_{197}$ was produced in *E. coli* cells as inclusion bodies (Stefan A, et al. J Biotechnol. December 20; 156(4):245-52, 2010; International Application Publication No. WO 2011/126811, Chinese Patent Application No. 200610042194) or as soluble protein directed to the periplasm by signal peptide (International Application Publication No. WO 2011/042516). The periplasm of *E. coli* is an oxidizing environment that allows the formation of disulfide bonds. CRM$_{197}$ has two disulfide bonds that are probably important for the correct folding and function, and for protein solubility.

It has been surprisingly discovered that a single, uncleaved chain of soluble recombinant CRM protein can be rapidly produced intracellularly and in commercial quantities from microorganisms and thereafter isolated and/or purified in large quantities and remain soluble. CRM is soluble in phosphate buffered saline (PBS, pH 7.5) and other similar buffers. Preferred CRM proteins produced are full length or partial regions such as, for example, peptides, single or multiple domains or epitopes, and any specific region expressed from native CRM coding sequences including CRM sequences that have been modified with one or more deletions, substitution and/or additions (e.g. conservative or non-conservative), and CRM sequences that have been modified with additional sequences (e.g., one or more promoters, start codons, and translation factor, ribosome or polymerase binding sites) that promote expression in a host organism. A preferred CRM protein is $CRM_{197}$. Preferred is expression of CRM protein that is soluble and not otherwise bound as insoluble inclusion bodies of the cell. Preferred expression systems for the expression and production of CRM proteins include microorganisms with an intracellular oxidative state. Preferred expression systems may be recombinant or native eukaryotic or prokaryotic cells wherein recombinant cells include cells that contain a non-native CRM coding sequence. Preferred prokaryotic cells are strains of *E. coli* or another bacterial strain that contains one or more genetic alterations (e.g., one or more deletions or mutations). Preferably the one or more genetic alterations shift the redox state of the cytoplasm of the cell to a more oxidative state, as compared to wild-type, for example as disclosed in U.S. Pat. No. 7,410,788 (which is incorporated by reference). Alterations preferably reduce the activity of one or more disulfide reductase genes and/or other genes that reduce the oxidative state of the cytoplasm. Preferably, reduced activity is due to non-expression or reduced expression of one, two or multiple disulfide reductase or other genes, or one or more mutations that reduce activity of one or more expressed disulfide reductase proteins or other proteins. Preferred strains of microbial cells (e.g., recombinant, engineered or native eukaryotic or prokaryotic cells) have increased abilities to produce natively folded proteins containing disulfide bonds yet remain as functional proteins. The method of the invention produces quantities of CRM proteins containing full, truncated or modified CRM amino acid sequences. Quantities of CRM protein produced according to the invention are surprising such as, for example, 600 mg or more of CRM protein per liter of bacterial cell culture.

One embodiment of the invention is directed to methods for the production of large quantities of CRM protein, and preferably $CRM_{197}$. Production quantities are typically quantified as mg/L of bacterial cell culture. CRM protein production, according to the methods of the invention, is 200 mg/L or more, 300 mg/L or more, 400 mg/L or more, 500 mg/L or more, 600 mg/L or more, 700 mg/L or more, 800 mg/L or more, 900 mg/L or more, 1,000 mg/L or more, 1,500 mg/L or more, or 2,000 mg/L or more. Preferred quantities $CRM_{197}$ of the invention includes related proteins containing full length and truncated CRM protein, as well as modified amino acid sequences of CRM protein. Modifications include one or more of conservative amino acid deletions, substitution and/or additions. A conservative modification is one that maintains the functional activity and/or immunogenicity of the molecule, although the activity and/or immunogenicity may be increased or decreased. Examples of conservative modifications of CRM include, but are not limited to amino acid modifications (e.g., single, double and otherwise short amino acid additions, deletions and/or substitutions), modifications outside of the 39 ε-amino groups of lysine (primary amine groups of lysine) residues that are accessible for conjugation in forming a vaccine, modifications due to serotype variations of DT, modifications that increase immunogenicity or increase conjugation efficiency, modification that do not substantially alter binding to heparin, modifications that maintain proper folding or three dimensional structure, and/or modifications that do not significantly alter immunogenicity of the protein or the portions of the protein that provide protective immunity to DT.

Recombinant cells that are used in the method of the invention are preferably *E. coli* bacteria and, preferably, *E. coli* that are genetically engineered to shift the redox state of the cytoplasm to a more oxidative state such as, for example, by mutation of one or more disulfide reductase genes such as, for example, an oxidoreductase, a dihydrofolate reductase, a thioredoxin reductase, a glutamate cysteine lyase, a disulfide reductase, a protein reductase, and/or a glutathione reductase. Preferably one or more disulfide reductase genes are mutated and rendered non-functional or marginally functional such that the redox state of the cytoplasm of the cell is shifted to a more oxidative state as compared to wild type. Oxidative protein folding involves the formation and isomerization of disulfide bridges and plays a key role in the stability and solubility of many proteins including CRM 197. Formation and the breakage of disulfide bridges is generally catalyzed by thiol-disulfide oxidoreductases. These enzymes are characterized by one or more Trx folds that consist of a four-stranded β-sheet surrounded by three α-helices, with a CXXC redox active-site motif. The assembly of various Trx modules has been used to build the different thiol oxidoreductases found in prokaryotic and in eukaryotic organisms. In the bacterial periplasm, the proteins are kept in the appropriate oxidation state by a combined action of the couples DsbB-DsbA and DsbD-DsbC/DsbE/DsbG (Inaba 2009, Gruber et al, 2006). Many protein expression systems are well known in the art and commercially available.

Especially preferred microbes include *E. coli* expression strains, for example, chemically competent *E. coli* K12 cells engineered to form disulfide bonded proteins in the cytoplasm (e.g., ORIGAMI™ (EMD Millipore) and SHUFFLE™ (New England Biolabs)). Other strains and types of cells and other *E. coli* strains with enhanced oxidative redox state also may be used. For example, ORIGAMI™ 2 host strains are K-12 derivatives that have mutations in both the thioredoxin reductase (trxB) and glutathione reductase (gor) genes, which greatly enhance disulfide bond formation in the *E. coli* cytoplasm. These strains are kanamycin sensitive; like the original Origami strains, the gor mutation is still selected for by tetracycline. To reduce the possibility of disulfide bond formation between molecules, strains containing mutations in trxB and gor are recommended only for the expression of proteins that require disulfide bond formation for proper folding. SHUFFLE™ cells are chemically competent *E. coli* K12 cells engineered to form proteins containing disulfide bonds in the cytoplasm. Preferably these cells contain mutations in trxB and gor and cytoplasmic chaperon disulfide bond isomerase DsbC (fhuA2 [lon] ompT ahpC gal λatt::pNEB3-r1-cDsbC (SpecR, $lacI^q$) ΔItrxB sulA11 R(mcr-73::miniTn10-$Tet^S$)2 [dcm] R(zgb-210::Tn10-$Tet^S$) endA1 Δgor A(mcrC-mrr)114::IS10). Also preferably, cells are suitable for T7 promoter driven protein expression and of the genotype F' lac, pro, lacIQ/Δ(ara-leu)7697 araD139 fhuA2 lacZ::T7 gene1 Δ(phoA)PvuII phoR ahpC* galE (or U) galK λatt::pNEB3-r1-cDsbC (Spec$^R$, lacI$^q$) ΔtrxB rpsL150(Str$^R$) Δgor Δ(malF)3. SHUFFLE™ strains expresses constitutively a chromosomal copy of the disufide bond isomerase DsbC. DsbC promotes the correction of mis-oxidized proteins into their correct form. Cytoplasmic DsbC is also a chaperone that can assist in the folding of proteins that do not require disulfide bonds.

Bacterial cultures are preferably cultured at temperatures such that solubility of the expressed protein increases (e.g., CRM or CRM$_{197}$) as compared to solubility at higher temperatures (e.g., 37° C.). Preferred culture temperatures are 30° C. or lower, preferably 25° C. or lower, preferably 20° C. or lower, preferably 18° C. or lower, and preferably between 15° C. and 32° C.

Another embodiment of the invention comprises recombinant cells such as, for example, bacterial, mammalian or insect cells containing expressible CRM sequences and, preferably sequences of CRM$_{197}$. Preferred host cells include, but are not limited to, cells genetically engineered to shift the redox state of the cytoplasm to a more oxidative state. Preferred cells include prokaryotic or eukaryotic cells such as, for example, E. coli cell expression systems, Baculovirus Expression System and other bacterial and/or eukaryotic cellular expression systems. Preferably the cells contain a protein expression system for expressing foreign or non-native sequences such as CRM peptides. Also preferable, the sequences to be expressed are comprised of an expression vector which contains one or more of an inducible promoter (e.g., auto-inducible preferably with specific media), a start codon (e.g., ATG), a ribosome binding site, and/or a modified sequence between ribosome binding site and ATG starting codon, or between start codon and the sequence to be expressed. Preferred modified sequences or spacer sequences include, for example, a number of nucleotides more or less than 9 (e.g., between 7 and 12 nucleotides), and preferably not 9 nucleotides. Specific examples of spacer nucleotides that can be utilized in an expression system include but are not limited to GATATAC (SEQ ID NO 3), GATATACCA (SEQ ID NO 4), and GATATACCATAT (SEQ ID NO 5). Accordingly, another embodiment of the invention comprises an expression construction of CRM, nucleotide and amino acids sequences, with or without defined spacer sequences and with and without a host cell.

Another embodiment of the invention is directed to recombinant CRM$_{197}$ protein and the expression of recombinant CRM in E. coli or another host cell using an expression vector with an inducible promoter and/or a modified sequence between ribosome binding site and ATG starting codon. Preferably, the expression vector includes the lactose/IPTG inducible promoter, preferably a tac promoter, and the sequence between ribosome binding site and ATG starting codon. Preferably the expression system contains a spacer between the start codon and the expression sequence which is comprised of a number of nucleotides more or less than 9 (e.g., between 7 and 12 nucleotides), and preferably not 9 nucleotides. Specific examples of spacer nucleotides that can be utilized in an expression system include but is not limited to those identified herein. It was surprisingly discovered that the use of spacers of length seven or twelve resulted in dramatically increased levels of CRM$_{197}$ expression when compared to spacers of nine nucleotides.

Another embodiment of the invention comprises an expression construction of CRM, nucleotide and amino acids sequences, with or without defined spacer sequences, as disclosed herein, and with or without an enhancer region. Enhancers regions promote protein expression by adding one or more sequences that promote nucleic acid recognition for increased expression (e.g., start codon, enzyme binding site, translation or transcription factor binding site). Preferably, an enhancer of the invention contains a ribosome binding site with a start codon upstream of and with a coding sequence that differs from the coding sequence of the CRM protein.

Another embodiment of the invention is directed to recombinant CRM, and in particular CRM$_{197}$, purified according to the methods of invention. Purification preferably comprises heparin or heparin-like affinity chromatography. It was surprisingly discovered that CRM$_{197}$ contains the sequence-based motif of typical heparin binding sites XBBXBX (SEQ. ID NO 6) where B is a lysine or arginine and X a hydropathic residue (Cardin A D, Weintraub H J., 1989: Molecular modeling of protein-glycosaminoglycan interactions. Arteriosclerosis 9: 21-32). This motif is located in the CRM$_{197}$ receptor-binding domain and comprises of the following amino acids: GRKIRMRCR (SEQ ID NO 7), where G (Glycine), I (Isoleucine), M (Methionine) and C (Cysteine) are hydropathic residues. Presence of heparin binding site allows the use of heparin or heparin-like resins in the purification. Heparin-like resins include resins containing functional sulfate groups, such as dextran sulfate, e.g. Dextran sulfate (Sterogene), Capto Devirs (GE) or sulfate esters, e.g. Cellufine Sulfate (Asahi Kasei Bioprocess).

In a first step, crude E. coli extract may be clarified, for example, preferably by centrifugation or depth filtration. Optionally cleared lysate may be fractionated further, preferably by adding salts that have effect on protein solubility and salting out CRM$_{197}$. In the second step, clarified lysate or re-solubilized salted out fraction containing CRM$_{197}$ may be applied, for example, to anion exchange resin under conditions when CRM$_{197}$ is in flow through. In the third step, the flow through fraction containing CRM$_{197}$ may be applied to a column. Preferred column resins include, but are not limited to dextran sulfate resins, CELLUFINE™ resins (Chisso Corporation; chromatography gel), active sulfated resins, phosphate resins, or heparin or heparin-like resins. Preferably binding of CRM to resin is performed in a low salt buffer and eluted in higher salt buffer, yielding highly purified CRM$_{197}$. Preferred binding buffers contain, for example, one or more ionic reagents and/or reagents that increase conductivity, one or more chaotropic agents, NaCl, KCl, glycerol, isopropyl alcohol, ethanol, arginine, acetate, guanidine, urea, ATP, one or more mono-, di-, tri-, and/or poly-phosphates, sulfates or pyrophosphates, and combinations thereof. Preferred elution buffers contain, for example, higher concentration of one or more components of the binding buffer.

Other preferred purification methods include any one or combination of an anion exchange chromatography, hydrophobic interaction chromatography and/or Cibacron-Blue resin (CN 101265288A, U.S. Pat. No. 8,383,783). Purification method of the invention produce recombinant CRM protein (e.g., CRM$_{197}$) at high yields, as discussed herein, and with a purity level of greater than 80%, preferably greater than 85%, preferably greater than 90%, preferably greater than 95%, preferably greater than 99%, and preferably with an even greater purity.

Another embodiment of the invention is directed to methods to characterize recombinant DT and CRM proteins (e.g., binding activity) and, in particular CRM$_{197}$, which contain a receptor binding domain (see SEQ ID NO 2). These methods comprise determination of the binding activity of proteins containing native or modified sequence of receptor binding domain of DT. Such modifications preferably preserve the ability of CRM to bind to HB-EGF (heparin binding epidermal growth factor). The method is applicable to both crude and purified $CRM_{197}$. Binding activity represents binding to the soluble form of diphtheria toxin receptor HB-EGF (DTR). Soluble forms are believed to be properly folded. These methods comprise, preferably, determining the binding $CRM_{197}$ to DTR and detection of with molecules (e.g., antibodies, antibody fragments, antigens) specific to the properly folded structure, the complex, binding, and/or the binding sites, and preferably in an ELISA format. Assays to determine and quantitate binding allow for the rapid determination that $CRM_{197}$ is correctly folded, as only properly folded $CRM_{197}$ binds to the receptor. Thus, the method monitors correct folding of manufactured $CRM_{197}$ and related proteins during the development, production and purification process. In addition, this characterization method can be used to identify and track CRM protein after conjugation with another molecule such as in vaccine production. Using the detection method of the invention, properly folded and configured conjugated CRM protein can be monitored during the development of a vaccine for the treatment and/or prevention of diseases and disorders in patients.

Another embodiment of the invention is directed to CRM and proteins and peptides related to CRM, as well as portions and domains thereof, that can be manufactured according to the method of the invention. Proteins and peptides related to CRM comprise, but are not limited to, for example, those proteins and peptides that can be cytoplasmically expressed without leader or tag sequences and at commercially significant levels according to the methods disclosed and described herein. Preferably, these proteins and peptides show proper folding upon expression in recombinant cells of the invention. Recombinant cells of the invention preferably show reduced activity of one or more disulfide reductase enzymes, preferable reduced activity of less than five disulfide reductase enzymes, preferable reduced activity of less than four disulfide reductase enzymes, and also preferable reduced activity of less than three disulfide reductase enzymes. Preferably expression of the proteins and peptides is increased in recombinant cells of the invention, but may be not reduced or not significantly reduced compared with expression in recombinant cell that does not have reduced activity of one or more disulfide reductase enzymes. Proteins and peptides that can be expressed in the methods disclosed herein include, but are not limited to, for example, tetanus toxin, tetanus toxin heavy chain proteins, diphtheria toxoid, tetanus toxoid, *Pseudomonas* exoprotein A, *Pseudomonas aeruginosa* toxoid, *Bordetella pertusis* toxoid, *Clostridium perfringens* toxoid, *Escherichia coli* heat-labile toxin B subunit, *Neisseria meningitidis* outer membrane complex, Hemophilus influenzae protein D, Flagellin Fli C, Horseshoe crab Haemocyanin, and fragments, derivatives, and modifications thereof.

Another embodiment of the invention is directed to CRM and proteins and peptides related to CRM, as well as portions and domains thereof, fused genetically or by chemical modification or conjugation (e.g., carbodiimide, 1-cyanodimethylaminopyridinium tetrafluoroborate (CDAP)) with another molecule. Preferred other molecules are molecules such as, but not limited to, other proteins, peptides, lipids, fatty acids, saccharides and/or polysaccharides, including molecules that extend half-life (e.g., PEG, antibody fragments such as Fc fragments), stimulate and/or increase immunogenicity, or reduce or eliminate immunogenicity. CRM contains an N-terminal serine which useful for conjugation. Typical conjugation partner molecules include, but are not limited to polymers such as, for example, bacterial polysaccharides, polysaccharides derived from yeast, parasite and/or other microorganisms, polyethylene glycol (PEG) and PEG derivatives and modifications, dextrans, and derivatives, modified, fragments and derivatives of dextrans. One example of a conjugation compound is the polymer PEGASYS® (peginterferon alfa-2a). Other polymers, such as dextran, also increase the half-life of proteins and reduce immunogenicity of the conjugate partner. Polymers may be linked randomly or directed through site specific conjugation such as, for example, by modification of N-terminal serines and/or threonines. Also modifications may be used that selectively oxidize chemical groups for site specific conjugation.

Another embodiment of the invention is directed to methods of producing a peptide containing a domain, fragment and/or portion of a CRM or related protein comprising: expressing the peptide from a recombinant cell containing an expression vector that encodes the peptide, wherein the recombinant cell has a reduced activity of one or more disulfide reductase enzymes and the expression vector contains a promoter functionally linked to a coding region of the peptide, wherein the one or more disulfide reductase enzymes comprises one or more of an oxidoreductase, a dihydrofolate reductase, a thioredoxin reductase, or a glutathione reductase; and isolating the peptide expressed, wherein the peptide expressed is soluble. Preferably the domain comprises a CRM receptor binding domain, a CRM catalytic toxic domain, and/or cytoplasmic transfer domain. Preferably the CRM receptor binding domain comprises the sequence of SEQ ID NO. 2. Preferably the expression vector contains a ribosome binding site, an initiation codon, and, optionally, an expression enhancer region. Preferably the recombinant cell has a reduced activity of only one disulfide reductase enzyme, only two disulfide reductase enzymes, or two or more disulfide reductase enzymes. Preferably the reduced activity of the disulfide reductase enzymes results in a shift the redox status of the cytoplasm to a more oxidative state as compared to a recombinant cell that does not have reduced activity of one or more disulfide reductase enzymes. Preferably the recombinant cell is an *E. coli* cell or a derivative or strain of *E. coli*. Preferably the expression vector contains at least one spacer between the ribosome binding site and the initiation codon. Preferably the soluble peptide expressed comprises a natively folded domain of CRM. The promoter may be a constitutive or inducible promoter, whereby expression comprises inducing the inducible promoter with an inducing agent. Preferred inducing agents include, for example, lactose (PLac), isopropyl β-D-1-thiogalactopyranoside (IPTG), substrates and derivative of substrates. In one preferred embodiment, the recombinant cell contains a second expression vector that preferably contains a coding region for a peptidase that preferably acts upon and selectively cleaves the peptide or protein expressed from the first expression vector. Preferably the second expression vector contains a second promoter functionally linked to the coding region, and co-expressing comprises expressing the peptide and the peptidase. The two expression vectors may be induced together with the same inducing agent, or with different inducing agents, optionally at different times. Preferably the peptidase acts on and cleaves the peptide co-expressed with the peptidase. Preferably the peptide expressed is conjugated with a polymer such as, for example, dextran, a bacterial capsular polysaccharide, polyethylene glycol (PEG), or a fragment, derivative or modification thereof. Preferably the peptide expressed is coupled with a polymer which includes, for example, a polysaccharide, a peptide, an antibody or portion of an antibody, a lipid, a fatty acid, or a combination thereof.

Another embodiment of the invention comprises methods of treating cancer patients by exposing cancels ells of the patients to the peptide of the invention. Preferably exposing reduces proliferation of cancer cells and/or inhibits angiogenesis. Preferably the peptide expressed binds to a receptor of the cancer cells such as, for example, the receptor is a heparin-binding EGF-like growth factor. Heparin-binding EGF-like growth factor (HB-EGF) is a member of the EGF family of growth factors that bind to and activate the EGF receptor. HB-EGF is synthesized as a membrane-anchored protein (proHB-EGF), and proteolytically cleaved, resulting in the mitogenically active soluble form. HB-EGF is implicated in cancer cell proliferation, malignancy, metastatic potential, and chemotherapy resistance. HB-EGF expression is elevated in many types of malignant tumors thus making HB-EGF a target for diagnosis and therapy of HB-EGF related cancers and related diseases. HB-EGF also serves as a receptor for diphtheria toxin (DT) and its mutant forms, including CRM197. Mutant form of DT and CRM prevent ectodomain shedding by binding to HB-EGF and represses mutagenic activity of HB-EGF. CRM induces only weak toxicity compare with DT and can involve an inflammatory response.

In another embodiment of the invention, it was surprisingly discovered that treatments with a domain of the invention conjugated or fused with a compound that increases half-life of the molecule increases effectiveness. The receptor binding domain of CRM197 (RBD CRM197, 381-535 aa) produced in recombinant cells according to this disclosure functions as an antitumor reagent and detection reagent in place of anti-HB-EGF monoclonal antibodies. Expressions of RBD CRM according to the disclosures herein (greater than 1 g/L) coupled with the purification disclosed herein makes RBD CRM197 an inexpensive reagent and tool for effective anticancer therapy. Binding of purified RBD CRM to human HB-EGF in plate based assay. Due to lack of A chain, RBD CRM197 does not produce toxicity as an anticancer drug. To increase the molecule blood permanence time and effectiveness, CRM receptor binding domain produced according to this disclosure is conjugated with dextran and utilized for antitumor drug delivery. Having serine as a first amino acid in the polypeptide chain allow for site specific conjugations which does not compromise HB-EGF binding. Conjugated to dextran to increase avidity and to HRP or dye for the detection RBD CRM is used to detect HG-EGF in IHC and plate based assays. The conjugate prevents HB-EGF binding to EGFR using ELISA format indicating that CRM according to this disclosure serves as a positive control and blocks EGFR phosphorylation and cell proliferation.

Another embodiment of the invention comprises conjugates of CRM and proteins related to CRM included fragments, domains, and portions thereof as disclosed and described herein.

Another embodiment of the invention comprises fusion molecules of CRM and proteins related to CRM included fragments, domains, and portions thereof as disclosed and described herein.

Another embodiment of the invention comprises a vaccine containing CRM and proteins related to CRM included fragments, domains, and portions thereof, as disclosed and described herein.

The following examples illustrate embodiments of the invention, but should not be viewed as limiting the scope of the invention.

EXAMPLES

Example 1. $CRM_{197}$ Expression Detected from Expression Vectors Containing 7 or 12 Nucleotides Sequence Between RBS and Initial ATG Codon but not 9 Nucleotides DNA encoded mature $CRM_{197}$ was cloned into three vectors containing tac promoter and various nucleotide spacing between RBS and initial ATG codon, in particular 7, 9 or 12 nucleotides. The expression vectors named pTac-CRM7, pTacCRM9 and pTacCRM12 were expressed in different E. coli strains, in particular ORIGAMI™ 2 cells, C41, High Control, Top 10. The SDS-PAGE analysis of the cells lysate shows that only pTacCRM7 and pTacCRM12 produce 58 kDa band corresponding to $CRM_{197}$.

Example 2. $CRM_{197}$ Expresses Soluble in Origami 2, E. coli Expression Strain that Allows Formation of Disulfide Bonds in the Cytoplasm $CRM_{197}$ was expressed insoluble at 37° C. When expression temperature was dropped below 37°, solubility of the protein expressed in ORIGAMI™ 2 cells and SHUFFLE™ cells, but not in the other tested E. coli strains, increases. $CRM_{197}$ is mostly soluble when expressed in ORIGAMI™ 2 cells at 18° C.

Example 3. Expression Enhancer Sequence (EES) in $CRM_{197}$ Expression

The EES promotes transcription of CRM sequence in a CRM-containing vector and results in polycistronic mRNA that translates into two proteins; a short EES peptide and a CRM peptide. The coding sequence of the native CRM gene was analyzed for potential 3D structure formation and found to contain a number of potential hairpins, which could inhibit translation. A CRM sequence was created that would potentially result in an mRNA with no hairpins structures yet translate the same CRM amino acid sequence. This gene sequence is referred to an optimized CRM sequence and comprises SEQ ID NO 8.

The optimized CRM sequence expresses well in both E. coli (e.g., BL21) and in E. coli engineered to contain an oxidized cytoplasm (e.g., Shuffle). CRM peptide translated from polycistronic mRNA produces a full length protein and is believed to be more stable than the native CRM coding sequence. Unlike the native CRM sequence, the optimized CRM sequence expressed as full-length and as a soluble protein in Shuffle cells. In addition, compared to native CRM, higher expression of the optimized CRM sequence was observed with a lower cell density and with increased binding to chromatography resin resulting in greater production levels of CRM protein.

Example 4. Ammonium Sulfate Precipitation of $CRM_{197}$ from Cell Lysate

SHUFFLE™ cells expressing $CRM_{197}$ were open using microfluidizer and 1M of sodium chloride was added to the cell lysate. To this was added enough ammonium sulfate to equal 1M followed by centrifugation for 30 minutes at 20,000× g, which removed mis-folded $CRM_{197}$ and most of the bacterial proteins. Following clarification the ammonium sulfate concentration was further increased to 2.2M. The precipitate, which is mainly $CRM_{197}$ was collected and re-solubilized in a low conductivity buffer.

Example 5. Purification of $CRM_{197}$ on a Heparin Column

Ammonium sulfate precipitated $CRM_{197}$ was resolubilized in 20 mM Tris-HCl pH 8.0 to achieve conductivity 5 mS/cm and loaded on an column containing Heparin Sepharose CL-68 resin (GE). The purification was performed under the following conditions: flow rate was 5 ml/min, wash buffer A: 20 mM Tris-HCl pH8. Elution was done with a buffer B 0-100% gradient, buffer B: buffer A+1M NaCl in 20 CV. Eluted $CRM_{197}$ was analyzed by SDS-PAGE in reduced and non-reduced conditions. The purity of eluted $CRM_{197}$ was greater than 95%. The protein reduced with DTT appears as a single polypeptide confirming that the intact form of $CRM_{197}$ is expressed in *E. coli.*

Example 6. Purification of $CRM_{197}$ on Capto Devirs Column

SHUFFLE™ cells expressing $CRM_{197}$ were open using microfluidizer in 1×PBS, pH7.4, 1% sodium pyrophosphate. The lysate was clarified using depth filtration. Clarified lysate was loaded on a column containing Q Sepharose XL (GE) and flow through fraction was collected. To reduce volume and conductivity flow through fraction was subjected to tangential flow filtration using 10K cassette (Sartorius). Capto Devirs resin was equilibrated with 25 mM sodium phosphate buffer, pH8.0. $CRM_{197}$ was bound to the column under the following conditions: conductivity was less than 10 mS/cm, in a binding buffer containing a chaotropic agent (e.g., in this case urea), wash buffer was 25 mM sodium phosphate, pH8.0. Elution was done with NaCl. Eluted $CRM_{197}$ was analyzed by SDS-PAGE under reduced and non-reduced conditions. The purity of eluted $CRM_{197}$ was greater than 95%. The protein reduced with DTT appears as a single polypeptide confirming that $CRM_{197}$ remains intact during purification process.

Example 7. Binding Assay for the $CRM_{197}$ Characterization

The recombinant soluble diphtheria toxin receptor HB-EGF (DTR) (Sigma) was bound to the ELISA plate. Blocking solution of 5% dry non-fat milk was used to prevent high background. Recombinant $CRM_{197}$ diluted in 1×PBS, pH7.4, 0.1% Twin 20 was incubated on the plate for 1 hour at 37° C. $CRM_{197}$ bound to HB-EGF was detected by rabbit polyclonal anti-$CRM_{197}$ antibody and goat anti-rabbit antibody conjugated to soybean peroxidase (Fina BioSolutions; Rockville, Md.). Denatured recombinant $CRM_{197}$ did not bind to the receptor.

Example 8. $CRM_{197}$ Produced in *E. coli* Binds to DTR Similarly to CRM from *Corynebacterium* and *Pseudomonas*

ELISA plates were coated with soluble HB-EGF and blocked with 5% dry non-fat milk. $CRM_{197}$ was bound to the receptor and detected with rabbit anti-$CRM_{197}$ polyclonal antibody and goat anti-rabbit polyclonal conjugated with SBP. $CRM_{197}$ expressed in *E. coli* showed the same affinity to HB-EGF as CRM produced in *Corynebacterium* and *Pseudomonas*.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. The term comprising, where ever used, is intended to include the terms consisting and consisting essentially of. Furthermore, the terms comprising, including, containing and the like are not intended to be limiting. It is intended that the specification and examples be considered exemplary only with the true scope and spirit of the invention indicated by the following claims.

Sequence ID Nos.

SEQ ID NO 1

```
GADDVVDSSK SFVMENFSSY HGTKPGYVDS IQKGIQKPKS GTQGNYDDDW
KEFYSTDNKY DAAGYSVDNE NPLSGKAGGV VKVTYPGLTK VLALKVDNAE
TIKKELGLSL TEPLMEQVGT EEFIKRFG DG ASRVVLSLPF AEGSSSEYI
NNWEQAKALS VELEINFE TR GKRGQDAMYE YMAQACAGNR VRRSVGSSLS
CINLDWDVIR DKTKTKIESL KEHGPIKNKM SESPNKTVSE EKAKQYLE EF
HQTALEHPEL SELKTVTGTN PVFAGANYAA WAVNVAQVID SETADNLEKT
TAALSILPGI GSVMGIADGA VHHNTEEIVA QSIALSSLMV AQAIPLVGEL
VDIGFAAYNF VESIINLF QV VHNSYNRPAY SPGHKTQPFL HDGYAVSWNT VEDSIIRT
GF QGESGHDIKI TAENTPLPIA GVLLPTIPGK LDVNKSKT HI SVNGRKIRMR
CRAIDGDVTF CRPKSPVYVG NGVHANLH VA FHRSSSEKIH SNEISSDSIG
VLGYQKTVDH TKVNSKLS LF FEIKS
```

SEQ ID NO 2

```
SPGHKTQPFL HDGYAVSWNT VEDSIIRT GF QGESGHDIKI TAENTPLPIA GVLLPTIPGK
LDVNKSKT HI SVNGRKIRMR CRAIDGDVTF CRPKSPVYVG NGVHANLH VA
FHRSSSEKIFI SNEISSDSIG VLGYQKTVDH TKVNSKLS LF FEIKS
```

SEQ ID NO 3

GATATAC

SEQ ID NO 4

GATATACCA

SEQ ID NO 5

GATATACCATAT

Sequence ID Nos.

SEQ ID NO 6

XBBXBX

SEQ ID NO 7

GRKIRMRCR

SEQ ID NO 8 Optimized CRM sequence

ATGGGTGCTGATGATGTTGTTGATTCCTCTAAGTCTTTCGTGATGGAAAATTTCTCGT
CCTATCACGGTACCAAGCCTGGCTATGTGGATAGCATTCAAAAGGGTATTCAAAAAC
CGAAGTCTGGTACCCAGGGCAACTACGATGACGATTGGAAAGAGTTTTACAGCACC
GACAACAAATATGACGCGGCAGGCTACAGCGTTGATAATGAAAATCCGCTGAGCGG
TAAGGCTGGCGGCGTCGTTAAGGTTACCTATCCGGGTCTGACGAAAGTGCTGGCCCT
GAAAGTTGACAATGCTGAAACCATCAAAAAAGAACTGGGTCTGAGCTTGACCGAGC
CGCTGATGGAACAGGTTGGTACTGAAGAATTCATTAAACGTTTTGGTGACGGCGCGA
GCCGTGTTGTGCTGTCCCTGCCGTTTGCCGAGGGTTCTAGCTCCGTGGAGTATATCA
ACAATTGGGAACAGGCGAAAGCGTTGAGCGTCGAGCTGGAAATCAATTTCGAGACT
CGTGGTAAGCGTGGCCAAGATGCGATGTACGAGTACATGGCCCAGGCATGTGCGGG
TAACCGCGTCCGTCGCAGCGTCGGCAGCTCCCTGAGCTGCATTAACCTGGACTGGGA
CGTGATCCGCGACAAGACTAAGACCAAGATTGAGAGCCTGAAAGAGCACGGTCCGA
TTAAGAACAAAATGTCCGAGTCTCCGAACAAAACGGTGAGCGAAGAAAAAGCCAA
ACAGTATCTGGAAGAATTCCATCAGACCGCCCTGGAGCACCCAGAGCTGAGCGAGC
TGAAAACCGTCACCGGCACGAATCCGGTTTTTGCGGGTGCGAACTACGCGGCATGG
GCAGTCAATGTTGCGCAAGTCATCGACAGCGAAACGGCTGATAACTTGGAGAAAAC
CACCGCGGCACTGAGCATTCTGCCGGGCATCGGTAGCGTTATGGGCATTGCGGACG
GTGCCGTGCATCACAATACCGAAGAAATTGTCGCGCAGAGCATCGCATTGTCTAGCC
TGATGGTTGCACAGGCCATTCCGCTGGTAGGCGAATTGGTGGATATCGGTTTCGCGG
CTTACAATTTCGTTGAGTCGATCATTAACCTGTTTCAAGTCGTTCACAATAGCTATAA
CCGTCCGGCATACAGCCCGGGTCATAAGACGCAACCGTTTCTGCATGATGGCTATGC
CGTGAGCTGGAACACGGTCGAGGATTCGATTATCCGTACCGGTTTTCAGGGTGAGAG
CGGTCACGACATCAAAATCACCGCGGAGAACACGCCGCTGCCTATTGCGGGCGTCC
TGCTGCCGACGATCCCGGGCAAACTGGACGTTAACAAGAGCAAGACCCATATCAGC
GTCAACGGTCGTAAGATTCGCATGCGTTGTCGTGCAATCGACGGTGACGTGACGTTC
TGCCGCCCAAAAAGCCCGGTGTACGTGGGTAACGGCGTGCACGCGAATCTGCATGT
CGCGTTCCACCGCTCCTCAAGCGAGAAAATCCACAGCAATGAAATTAGCAGCGACA
GCATTGGTGTGTTGGGCTACCAAAAGACCGTGGATCACACCAAGGTTAATAGCAAG
CTGAGCCTGTTCTTTGAGATCAAAAGC

SEQ ID NO 9 Not optimized CRM sequence

ATGGGTGCCGATGACGTGGTTGACTCTTCCAAAAGCTTCGTCATGGAAAACTTCAGC
TCCTATCACGGCACTAAACCGGGTTATGTCGACAGCATCCAGAAAGGCATCCAGAA
ACCGAAATCTGGCACTCAGGGTAACTATGACGACGACTGGAAAGAGTTCTACTCTA
CCGACAACAAATACGACGCGGCTGGTTATTCTGTGGACAACGAAAACCCGCTGTCT
GGTAAAGCTGGTGGTGTTGTTAAAGTGACCTACCCGGGTCTGACCAAAGTTCTGGCT
CTGAAAGTGGACAACGCCGAAACCATCAAAAAAGAACTGGGTCTGTCTCTGACCGA
ACCGCTGATGGAACAGGTAGGTACCGAGGAATTCATCAAACGTTTTGGTGATGGTG
CGTCCCGTGTTGTACTGTCTCTGCCATTTGCCGAAGGTTCTAGCTCTGTCGAGTACAT
CAACAACTGGGAGCAGGCCAAAGCTCTGTCTGTGGAACTGGAAATCAACTTCGAGA
CCCGTGGTAAACGTGGTCAGGACGCAATGTATGAATACATGGCACAGGCTTGCGCG
GGTAACCGTGTACGTCGTTCTGTAGGTTCTTCCCTGTCTTGCATCAACCTGGACTGGG
ATGTCATCCGTGACAAAACCAAAACCAAAATCGAGTCCCTGAAAGAGCACGGTCCG
ATCAAAAACAAAATGAGCGAATCTCCGAACAAAACGGTCTCTGAGGAAAAAGCGA
AACAGTACCTGGAAGAATTCCATCAGACCGCCCTGGAACACCCGGAACTGTCTGAA
CTGAAAACCGTTACCGGTACTAACCCGGTTTTCGCAGGTGCTAACTACGCAGCGTGG
GCGGTTAACGTAGCCCAGGTAATCGATTCCGAAACCGCAGACAACCTGGAAAAAAC
GACTGCGGCTCTGTCTATTCTGCCGGGTATTGGTAGCGTGATGGGTATTGCAGATGG
TGCAGTTCACCACAACACGGAAGAAATCGTTGCGCAGTCTATCGCTCTGTCTTCTCT
GATGGTAGCACAGGCGATCCCGCTGGTTGGTGAACTGGTTGACATTGGCTTCGCGGC
CTACAACTTCGTTGAATCCATCATCAACCTGTTCCAGGTTGTGCACAACTCTTACAAC
CGTCCAGCTTACTCTCCGGGTCACAAAACCCAGCCGTTCCTGCACGACGGTTATGCG
GTTTCTTGGAACACCGTTGAAGACAGCATCATCCGTACTGGTTTCCAGGGTGAATCT
GGCCACGACATCAAAATCACTGCTGAAAACACCCCGCTGCCGATCGCAGGTGTTCTC
CTGCCAACTATTCCGGGTAAACTGGACGTGAACAAATCCAAAACGCACATCTCCGT
GAACGGTCGTAAAATCCGCATGCGTTGTCGTGCGATTGATGGTGACGTTACTTTCTG
TCGTCCGAAATCTCCGGTCTACGTAGGTAACGGTGTACATGCTAACCTCCATGTAGC
GTTCCACCGTTCTTCTTCCGAGAAAATCCACTCCAACGAGATCTCTAGCGACTCTAT
CGGTGTTCTGGGTTACCAGAAAACCGTTGACCACACCAAAGTGAACTCCAAACTCA
GCCTGTTCTTCGAAATCAAATCT

SEQ ID NO 10 crm 7

GAGCTCTAAGAAGGA<u>GATATAC</u>ATGGGTGCCGATGACGTGGTTGACTCT

SEQ ID NO 11 crm 7_2

GAGCTCTTAAGAAGGA<u>GATATAC</u>ATGGGTGCCGATGACGTGGTTGACTCT

SEQ ID NO 12 crm 8

GAGCTCTAAGAAGGA<u>GATATACA</u>ATGGGTGCCGATGACGTGGTTGACTCT

| Sequence ID Nos. |
| --- |

SEQ ID NO 13 crm 9
GAGCTCTAAGAAGGA<u>AGATATACAC</u>ATGGGTGCCGATGACGTGGTTGACTCT SEQ ID NO 14 crm 12
GAGCTCTAAGAAGGA<u>AGATATACCATAT</u>ATGGGTGCCGATGACGTGGTTGACTCT SEQ ID NO 15
TCTAGAAATAATTTTGTTTAACTTTAAGAAGGAGATATACATATGGCTAGCATGACT
GGTGGACAGCAAATGGGTCGGGATCCGAATTCGAGCTCTAAGAAGGAGATATACC SEQ ID NO 16
TCTAGAAATAATTTTGTTTAACTTTAAGAAGGAGATATACATATGGCTAGCATGACT
GGTAAGGAGATATACC SEQ ID NO 17
TCTAGAAATAATTTTGTTTAACTTTAAGAAGGAGATATACATATGGCTAGCATGACT
GGTGCGMAYCCATTCAGTGAAGAAGRAGSTTYATT<u>T</u>

---

The invention claimed is:

1. A method of producing a peptide containing a domain of a cross reactive materials protein (CRM) comprising:
   expressing the peptide from a recombinant cell containing an expression vector that encodes the peptide, wherein the recombinant cell has a reduced activity of one or more disulfide reductase enzymes and the expression vector contains a promoter functionally linked to a coding region of the peptide, wherein:

the one or more disulfide reductase enzymes comprises one or more of an oxidoreductase, a dihydrofolate reductase, a thioredoxin reductase, or a glutathione reductase, and the peptide is expressed cytoplasmically; and isolating the peptide expressed, wherein the peptide expressed is soluble.

2. The method of claim 1, wherein the domain comprises a CRM receptor binding domain.

3. The method of claim 2, wherein the CRM receptor binding domain comprises the sequence of SEQ ID NO. 2.

4. The method of claim 1, wherein the domain comprises a CRM catalytic toxic domain.

5. The method of claim 1, wherein the domain comprises a CRM cytoplasmic transfer domain.

6. The method of claim 1, wherein the expression vector contains a ribosome binding site, an initiation codon, and an expression enhancer region.

7. The method of claim 1, wherein the recombinant cell has a reduced activity of only one disulfide reductase enzyme.

8. The method of claim 1, wherein the recombinant cell has a reduced activity of only two disulfide reductase enzymes.

9. The method of claim 1, wherein the reduced activity of one or more disulfide reductase enzymes results in a shift the redox status of the cytoplasm to a more oxidative state as compared to a recombinant cell that does not have reduced activity of one or more disulfide reductase enzymes.

10. The method of claim 1, wherein the recombinant cell is an *Escherichia coli* cell or a derivative or strain of *Escherichia coli.*

11. The method of claim 1, wherein the expression vector contains at least one spacer between the ribosome binding site and the initiation codon.

12. The method of claim 1, wherein the soluble peptide expressed comprises a natively folded domain of CRM.

13. The method of claim 1, wherein the promoter is an inducible promoter and expressing comprises inducing the inducible promoter with a first inducing agent.

14. The method of claim 13, wherein the first inducing agent comprises lactose and/or isopropyl β-D-1-thiogalactopyranoside (IPTG).

15. The method of claim 13, wherein the recombinant cell contains a second expression vector.

16. The method of claim 15, wherein the second expression vector contains a coding region for a peptidase.

17. The method of claim 16, wherein the second expression vector contains a second promoter functionally linked to the coding region, and expressing comprises expressing the peptide and the peptidase.

18. The method of claim 17, further comprising cleaving the peptide expressed with the peptidase expressed.

19. The method of claim 17, wherein the second promoter is a constitutive promoter.

20. The method of claim 17, wherein the second promoter is a second inducible promoter and expressing comprises inducing the second inducible promoter with a second inducing agent.

21. The method of claim 20, wherein the second inducing agent comprises lactose and/or isopropyl β-D-1-thiogalactopyranoside (IPTG).

22. The method of claim 20, wherein the first inducing agent and the second inducing agent are different.

23. The method of claim 1, wherein expressing comprises propagating the recombinant cell at a temperature from about 15° C. to about 37° C.

24. The method of claim 1, wherein isolating comprises chromatography.

25. The method of claim 24, wherein the chromatography comprises a sulfate resin, a gel resin, an active sulfated resin, a phosphate resin, a heparin resin or a heparin-like resin.

26. The method of claim 1, further comprising conjugating the peptide expressed with polyethylene glycol and/or a derivative of polyethylene glycol.

27. The method of claim 1, further comprising coupling the peptide expressed with a polymer.

28. The method of claim 27, wherein the polymer comprises a polysaccharide, a peptide, an antibody or portion of an antibody, a lipid, a fatty acid, or a combination thereof.

29. The method of claim 1, further comprising exposing the peptide expressed to cancer cells.

30. The method of claim 29, wherein exposing reduces proliferation of cancer cells.

31. The method of claim 29, wherein the peptide expressed binds to a receptor of the cancer cells.

32. The method of claim 31, wherein the receptor is a heparin-binding EGF-like growth factor.

33. A method of producing a peptide containing a domain of a CRM protein comprising:
  expressing the peptide from a recombinant cell containing an expression vector that encodes the peptide, wherein the recombinant cell has a reduced activity of one or more disulfide reductase enzymes and the expression vector contains a promoter functionally linked to a coding region of the peptide, wherein:
    the reduced activity of one or more disulfide reductase enzymes results in a shift the redox status of the cytoplasm to a more oxidative state as compared to a recombinant cell that does not have reduced activity of one or more disulfide reductase enzymes, and the peptide is expressed cytoplasmically; and
  isolating the peptide expressed, wherein the peptide expressed is soluble.

34. The method of claim 33, wherein the domain comprises a CRM receptor binding domain.

35. The method of claim 34, wherein the CRM receptor binding domain comprises the sequence of SEQ ID NO. 2.

36. The method of claim 33, wherein the domain comprises a CRM catalytic toxic domain.

37. The method of claim 33, wherein the domain comprises a CRM cytoplasmic transfer domain.

38. The method of claim 33, wherein the expression vector contains a ribosome binding site, an initiation codon, and an expression enhancer region.

39. The method of claim 33, wherein the recombinant cell has a reduced activity of only one disulfide reductase enzyme.

40. The method of claim 33, wherein the recombinant cell has a reduced activity of only two disulfide reductase enzymes.

41. The method of claim 33, wherein the one or more disulfide reductase enzymes comprises one or more of an oxidoreductase, a dihydrofolate reductase, a thioredoxin reductase, or a glutathione reductase.

42. The method of claim 33, wherein the recombinant cell is an *Escherichia coli* cell or a derivative or strain of *Escherichia coli*.

43. The method of claim 33, wherein the soluble peptide expressed comprises a natively folded domain of CRM.

44. The method of claim 33, wherein the promoter is an inducible promoter and expressing comprises inducing the inducible promoter with a first inducing agent.

45. The method of claim 44, wherein the first inducing agent comprises lactose and/or isopropyl β-D-1-thiogalactopyranoside (IPTG).

46. The method of claim 33, wherein isolating comprises chromatography.

47. The method of claim 46, wherein the chromatography comprises a sulfate resin, a gel resin, an active sulfated resin, a phosphate resin, a heparin resin or a heparin-like resin.

48. The method of claim 33, further comprising conjugating the peptide expressed with polyethylene glycol (PEG) and/or a derivative of PEG.

49. The method of claim 33, further comprising coupling the peptide expressed with a polymer.

50. The method of claim 49, wherein the polymer comprises a polysaccharide, a peptide, an antibody or portion of an antibody, a lipid, a fatty acid, or a combination thereof.

51. The method of claim 33, further comprising exposing the peptide expressed to cancer cells.

52. The method of claim 51, wherein exposing reduces proliferation of cancer cells.

53. The method of claim 51, wherein the peptide expressed binds to a receptor of the cancer cells.

54. The method of claim 53, wherein the receptor is a heparin-binding EGF-like growth factor receptor.

55. A method of producing a peptide containing a domain of a toxoid protein comprising:

expressing the peptide from a recombinant cell containing an expression vector that encodes the peptide, wherein the recombinant cell has a reduced activity of one disulfide reductase enzyme that shifts the redox status of the cytoplasm to a more oxidative state as compared to a recombinant cell that does not have reduced activity of one disulfide reductase enzyme, and the expression vector contains a promoter functionally linked to a coding region of the peptide, wherein:

one disulfide reductase enzyme comprises an oxidoreductase, a dihydrofolate reductase, a thioredoxin reductase, or a glutathione reductase; and the peptide is expressed cytoplasmically; and isolating the peptide expressed, wherein the peptide expressed is soluble.

56. The method of claim 55, wherein the domain comprises a CRM receptor binding domain.

57. The method of claim 56, wherein the CRM receptor binding domain comprises the sequence of SEQ ID NO. 2.

58. The method of claim 55, wherein the domain comprises a CRM catalytic toxic domain.

59. The method of claim 55, wherein the domain comprises a CRM cytoplasmic transfer domain.

60. The method of claim 55, wherein the domain comprises a tetanus toxoid domain.

61. The method of claim 55, wherein the domain comprises a pertusis toxoid domain.

62. The method of claim 55, further comprising conjugating the peptide expressed with polyethylene glycol (PEG) and/or a derivative of PEG.

63. The method of claim 55, further comprising coupling the peptide expressed with a polymer.

64. The method of claim 63, wherein the polymer comprises a polysaccharide, a peptide, an antibody or portion of an antibody, a lipid, a fatty acid, or a combination thereof.

65. The method of claim 55, further comprising exposing the peptide expressed to cancer cells.

66. The method of claim 65, wherein exposing reduces proliferation of cancer cells.

67. The method of claim 65, wherein the peptide expressed binds to a receptor of the cancer cells.

68. The method of claim 67, wherein the receptor is a heparin-binding EGF-like growth factor receptor.

* * * * *

SEQUENCE LISTING

<160> NUMBER OF SEQ ID NOS: 17

<210> SEQ ID NO 1
<211> LENGTH: 535
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly

```
            210                 215                 220
Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
        435                 440                 445

His Ile Ser Val Asn Gly Arg Lys Ile Arg Met Arg Cys Arg Ala Ile
    450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
                485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
        515                 520                 525

Leu Phe Phe Glu Ile Lys Ser
        530                 535

<210> SEQ ID NO 2
<211> LENGTH: 155
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ser Pro Gly His Lys Thr Gln Pro Phe Leu His Asp Gly Tyr Ala Val
1               5                   10                  15

Ser Trp Asn Thr Val Glu Asp Ser Ile Ile Arg Thr Gly Phe Gln Gly
            20                  25                  30
```

```
Glu Ser Gly His Asp Ile Lys Ile Thr Ala Glu Asn Thr Pro Leu Pro
         35                  40                  45

Ile Ala Gly Val Leu Leu Pro Thr Ile Pro Gly Lys Leu Asp Val Asn
 50                  55                  60

Lys Ser Lys Thr His Ile Ser Val Asn Gly Arg Lys Ile Arg Met Arg
 65                  70                  75                  80

Cys Arg Ala Ile Asp Gly Asp Val Thr Phe Cys Arg Pro Lys Ser Pro
                 85                  90                  95

Val Tyr Val Gly Asn Gly Val His Ala Asn Leu His Val Ala Phe His
            100                 105                 110

Arg Ser Ser Ser Glu Lys Ile His Ser Asn Glu Ile Ser Ser Asp Ser
        115                 120                 125

Ile Gly Val Leu Gly Tyr Gln Lys Thr Val Asp His Thr Lys Val Asn
130                 135                 140

Ser Lys Leu Ser Leu Phe Phe Glu Ile Lys Ser
145                 150                 155
```

<210> SEQ ID NO 3
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3 gatatac                                                                7

<210> SEQ ID NO 4
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4 gatatacca                                                              9

<210> SEQ ID NO 5
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gatataccat at                                                         12

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any hydropathic residue
<220> FEATURE:
<221> NAME/KEY: MOD_RES
<222> LOCATION: (2)..(3)
<223> OTHER INFORMATION: Lys or Arg

```
<220> FEATURE:
<221> NAME/KEY: MOD_RES
<222> LOCATION: (4)..(4)
<223> OTHER INFORMATION: Any hydropathic residue
<220> FEATURE:
<221> NAME/KEY: MOD_RES
<222> LOCATION: (5)..(5)
<223> OTHER INFORMATION: Lys or Arg
<220> FEATURE:
<221> NAME/KEY: MOD_RES
<222> LOCATION: (6)..(6)
<223> OTHER INFORMATION: Any hydropathic residue

<400> SEQUENCE: 6

Xaa Xaa Xaa Xaa Xaa Xaa
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Arg Lys Ile Arg Met Arg Cys Arg
1               5

<210> SEQ ID NO 8
<211> LENGTH: 1608
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
atgggtgctg atgatgttgt tgattcctct aagtctttcg tgatggaaaa tttctcgtcc      60
tatcacggta ccaagcctgg ctatgtggat agcattcaaa agggtattca aaaaccgaag     120
tctggtaccc agggcaacta cgatgacgat tggaaagagt tttacagcac cgacaacaaa     180
tatgacgcgg caggctacag cgttgataat gaaaatccgc tgagcggtaa ggctggcggc     240
gtcgttaagg ttacctatcc gggtctgacg aaagtgctgg ccctgaaagt tgacaatgct     300
gaaaccatca aaaagaact gggtctgagc ttgaccgagc cgctgatgga acaggttggt     360
actgaagaat tcattaaacg ttttggtgac ggcgcgagcc gtgttgtgct gtccctgccg     420
tttgccgagg ttctagctc cgtggagtat atcaacaatt gggaacaggc gaaagcgttg     480
agcgtcgagc tggaaatcaa tttcgagact cgtggtaagc gtggccaaga tgcgatgtac     540
gagtacatgg cccaggcatg tgcgggtaac cgcgtccgtc gcagcgtcgg cagctccctg     600
agctgcatta acctggactg ggacgtgatc cgcgacaaga ctaagaccaa gattgagagc     660
ctgaaagagc acggtccgat taagaacaaa atgtccgagt ctccgaacaa acggtgagc     720 gaagaaaaag ccaaacagta tctggaagaa ttccatcaga ccgccctgga gcacccagag     780
ctgagcgagc tgaaaaccgt caccggcacg aatccggttt tgcgggtgc gaactacgcg     840 gcatgggcag tcaatgttgc gcaagtcatc gacagcgaaa cggctgataa cttggagaaa     900
accaccgcgg cactgagcat tctgccgggc atcggtagcg ttatgggcat gcggacggt     960 gccgtgcatc acaataccga agaaattgtc gcgcagagca tcgcattgtc tagcctgatg    1020
gttgcacagg ccattccgct ggtaggcgaa ttggtggata tcggtttcgc ggcttacaat    1080
```

```
ttcgttgagt cgatcattaa cctgtttcaa gtcgttcaca atagctataa ccgtccggca   1140
tacagcccgg gtcataagac gcaaccgttt ctgcatgatg gctatgccgt gagctggaac   1200
acggtcgagg attcgattat ccgtaccggt tttcagggtg agagcggtca cgacatcaaa   1260
atcaccgcgg agaacacgcc gctgcctatt gcgggcgtcc tgctgccgac gatcccgggc   1320
aaactggacg ttaacaagag caagacccat atcagcgtca acggtcgtaa gattcgcatg   1380
cgttgtcgtg caatcgacgg tgacgtgacg ttctgccgcc caaaaagccc ggtgtacgtg   1440
ggtaacggcg tgcacgcgaa tctgcatgtc gcgttccacc gctcctcaag cgagaaaatc   1500
cacagcaatg aaattagcag cgacagcatt ggtgtgttgg gctaccaaaa gaccgtggat   1560
cacaccaagg ttaatagcaa gctgagcctg ttctttgaga tcaaaagc               1608

<210> SEQ ID NO 9
<211> LENGTH: 1608
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
atgggtgccg atgacgtggt tgactcttcc aaaagcttcg tcatggaaaa cttcagctcc     60
tatcacggca ctaaaccggg ttatgtcgac agcatccaga aaggcatcca gaaaccgaaa    120
tctggcactc agggtaacta tgacgacgac tggaaagagt tctactctac cgacaacaaa    180
tacgacgcgg ctggttattc tgtggacaac gaaaacccgc tgtctggtaa agctggtggt    240
gttgttaaag tgacctaccc gggtctgacc aaagttctgg ctctgaaagt ggacaacgcc    300
gaaaccatca aaaagaact gggtctgtct ctgaccgaac cgctgatgga acaggtaggt    360
accgaggaat tcatcaaacg ttttggtgat ggtgcgtccc gtgttgtact gtctctgcca    420
tttgccgaag ttctagctc tgtcgagtac atcaacaact gggagcaggc caaagctctg    480
tctgtggaac tggaaatcaa cttcgagacc cgtggtaaac gtggtcagga cgcaatgtat    540
gaatacatgg cacaggcttg cgcgggtaac cgtgtacgtc gttctgtagg ttcttccctg    600
tcttgcatca acctggactg ggatgtcatc cgtgacaaaa ccaaaaccaa atcgagtcc    660 ctgaaagagc acggtccgat caaaaacaaa atgagcgaat ctccgaacaa aacggtctct    720
gaggaaaaag cgaaacagta cctggaagaa ttccatcaga ccgccctgga cacccggaa    780 ctgtctgaac tgaaaaccgt taccggtact aacccggttt cgcaggtgc taactacgca    840 gcgtgggcg ttaacgtagc ccaggtaatc gattccgaaa ccgcagacaa cctggaaaaa    900
acgactgcgg ctctgtctat tctgccgggt attggtagcg tgatgggtat tgcagatggt    960
gcagttcacc acaacacgga agaaatcgtt gcgcagtcta tcgctctgtc ttctctgatg   1020
gtagcacagg cgatcccgct ggttggtgaa ctggttgaca ttggcttcgc ggcctacaac   1080
ttcgttgaat ccatcatcaa cctgttccag gttgtgcaca actcttacaa ccgtccagct   1140
tactctccgg gtcacaaaac ccagccgttc ctgcacgacg ttatgcggt ttcttggaac    1200 accgttgaag acagcatcat ccgtactggt ttccagggtg aatctggcca cgacatcaaa   1260
atcactgctg aaaacacccc gctgccgatc gcagtgttc cctgccaac tattccgggt    1320 aaactggacg tgaacaaatc caaaacgcac atctccgtga acggtcgtaa aatccgcatg   1380
cgttgtcgtg cgattgatgg tgacgttact ttctgtcgtc cgaaatctcc ggtctacgta   1440
ggtaacggtg tacatgctaa cctccatgta gcgttccacc gttcttcttc cgagaaaatc   1500
```
cactccaacg agatctctag cgactctatc ggtgttctgg gttaccagaa aaccgttgac    1560
cacaccaaag tgaactccaa actcagcctg ttcttcgaaa tcaaatct    1608

<210> SEQ ID NO 10
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gagctctaag aaggagatat acatgggtgc cgatgacgtg gttgactct    49

<210> SEQ ID NO 11
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gagctcttaa gaaggagata tacatgggtg ccgatgacgt ggttgactct    50

<210> SEQ ID NO 12
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gagctctaag aaggagatat acaatgggtg ccgatgacgt ggttgactct    50

<210> SEQ ID NO 13
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gagctctaag aaggagatat acacatgggt gccgatgacg tggttgactc t    51

<210> SEQ ID NO 14
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gagctctaag aaggagatat accatatatg ggtgccgatg acgtggttga ctct    54

<210> SEQ ID NO 15
<211> LENGTH: 112
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

```
tctagaaata attttgttta actttaagaa ggagatatac atatggctag catgactggt      60
ggacagcaaa tgggtcggga tccgaattcg agctctaaga aggagatata cc             112

<210> SEQ ID NO 16
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tctagaaata attttgttta actttaagaa ggagatatac atatggctag catgactggt      60
aaggagatat acc                                                        73

<210> SEQ ID NO 17
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tctagaaata attttgttta actttaagaa ggagatatac atatggctag catgactggt      60
gcgmayccat tcagtgaaga agragsttya ttt                                  93
```